March 12, 1963 C. FISCHER Plant Pat. 2,236
GLADIOLUS PLANT
Filed April 12, 1962
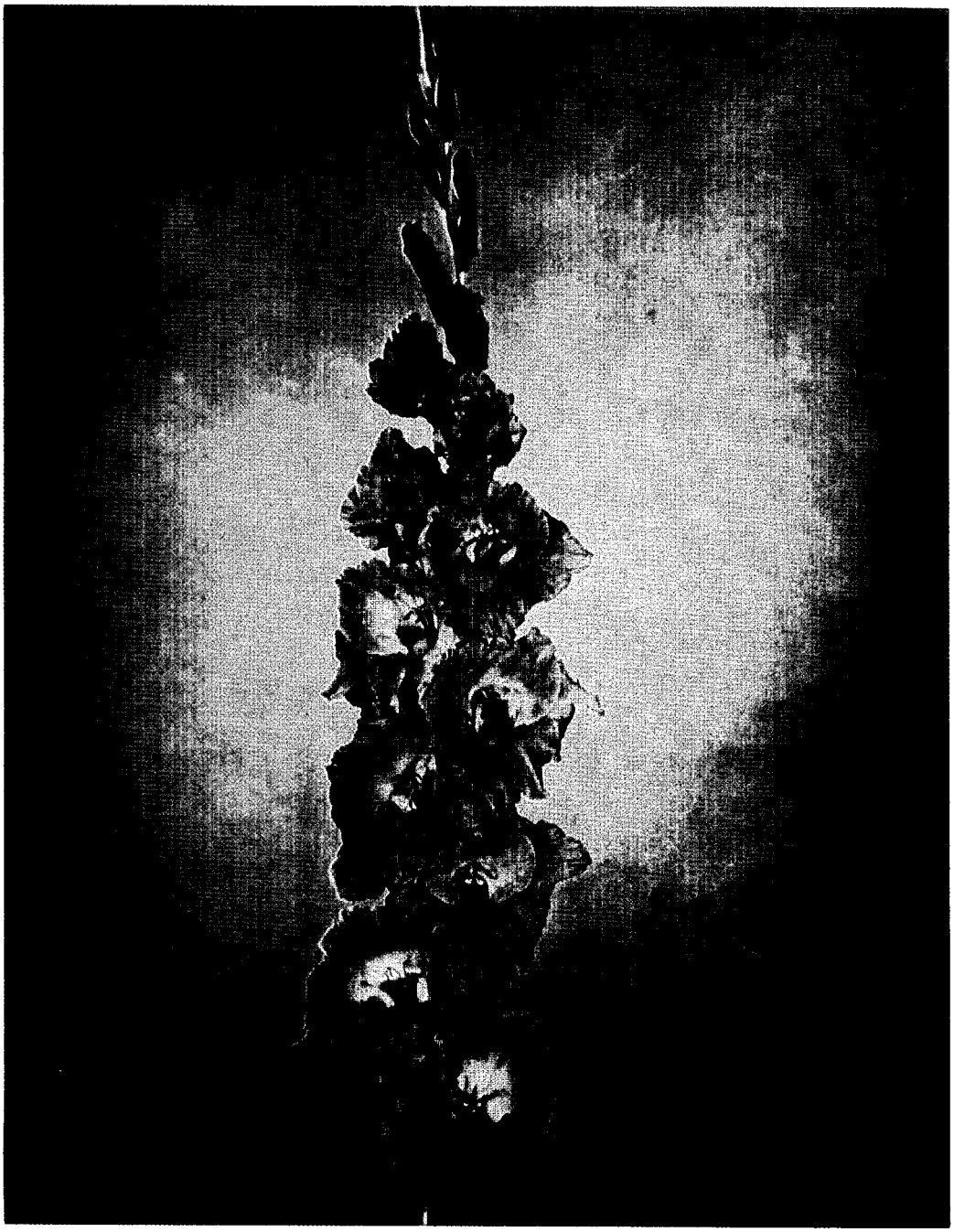
Inventor.
Carl Fischer
By: Robb & Robb
Attorneys.

United States Patent Office

Plant Pat. 2,236
Patented Mar. 12, 1963

2,236
GLADIOLUS PLANT

Carl Fischer, St. Charles, Minn., assignor to Imperial Flowers Limited, Leamington, Ontario, Canada, a corporation of Canada Filed Apr. 12, 1962, Ser. No. 187,143
1 Claim. (Cl. 47—60)

The present invention relates to a new and distinct variety of Gladiolus plant which was originated by me by crossing the variety "Fire Gleam" (unpatented) with the variety "Purple Burma" (unpatented), the former being the seed parent and the latter being the pollen parent.

As the result of this breeding, I have produced a new gladiolus variety which is distinguished from its parents, as well as from all other varieties of which I am aware, as evidenced by the following unique combination of characteristics which are outstanding therein and which represent a commercially valuable and desirable combination of features:

(1) A precise styling of the flowers;
(2) Heavy flower petal substance;
(3) An extremely ruffled form of the flowers; and
(4) A distinctive and attractive brilliant purple general color tonality of the flowers .

My new variety resembles the parent "Purple Burma" more than any other known variety, but differs therefrom principally by being a healthier variety; and earlier bloomer; a heavier flower substance; a more ruffled flower form; a more rosy flower color; and a richer and more velvety flower throat.

Asexual reproduction of the new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging form closed buds through paritally open buds to fully open flowers, as depicted in color as nearly true as it is reasonably possible to make the same in a color illustration of this character.

The following is a detailed description of my new variety, with color terminology in accordance with the Horticultural Colour Charts isued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Strong; prolific; blossom spike attains height averaging from 54 inches to 58 inches.

Blooming habit: Mid-season bloomer in the northern latitudes of the United States; comes into bloom from the planting of large bulbs in about 80 days.

Stems: Willowy.
*Diameter at base.*—⅜ inch.
*Color (just above the bulb).*—Light rose purple, stem shades to brownish at reverse of flower head.

Foliage: Attains height of about 36 inches, with leaves slightly drooping; leaves range from 1 inch to 1¼ inches wide. Color—green.

Disease Resistance: Unusually resistant to Fusarium yellows, Sclerotina dry rot and Septoria leaf spot, as determined by comparison with other varieties grown in my fields near St. Charles, Minnesota, in irrigated black loam soil.

Corms (bulbs): Normal, with reddish cast on husk. Color of flesh—Brick Red, Plate 016/2.

*Flower*

Spike: Average height; bears from 18 to 20 buds, with from 7 to 9 buds opening at once and with 6 or 7 buds showing color.

Bud:
Size.—About 3½ inches long when opening; buds taper in size toward tip.
*Opening.*—6 or 7 buds show color at one time.

Flower:
*Arrangement.*—Florets are formally arranged in a double row on the stem and usually all face forward.
*Size.*—Individual florets measure about 5½ inches in diameter, with upper blooms being progressively smaller.
*Form.*—Florets are round and extremely ruffled.
*Keeping qualities.*—Poor opener from tight bud.

Petals:
*Shape.*—Broad; round; recurved.
*Size.*—Outer petals—about 2½ inches wide. Lip petal—about 1⅞ inches wide.
*Aspect.*—Extremely heavy substance; leathery; smooth surface.
*Fragrance.*—None.
*Color.*—Dianthus Purple, Plate 730/1, shading to Dianthus Purple, Plate 730 on edges and on blotch, with upper petals shading to Dianthus Purple, Plate 730/3 at heart of flower, and reverse of petals being intense Dianthus Purple, Plate 730.

*Reproductive Organs*

Stamens: Color—Spectrum Violet, Plate 735/2.
Pistle: Color—Dianthus Purple, Plate 730/3.

I claim:

A new and distinct variety of gladiolus plant, substantially as herein shown and described, characterized particularly as to novelty by the unique combination of a precise flower styling, a heavy flower petal substance, an extremely ruffled flower form, and a distinctive and attractive brilliant purple general color tonality of the flowers.

No references cited.